(12) United States Patent
Thomson et al.

(10) Patent No.: US 8,012,751 B2
(45) Date of Patent: Sep. 6, 2011

(54) DIFFERENTIATION OF PLURIPOTENT EMBRYONIC STEM CELLS

(75) Inventors: James A. Thomson, Madison, WI (US); Thomas P. Zwaka, Pearland, TX (US)

(73) Assignee: Wisconsin Alumni Research Foundation, Madison, WI (US)

( * ) Notice: Subject to any disclaimer, the term of this patent is extended or adjusted under 35 U.S.C. 154(b) by 558 days.

(21) Appl. No.: 11/395,657

(22) Filed: Mar. 31, 2006

(65) Prior Publication Data

US 2006/0223179 A1 Oct. 5, 2006

Related U.S. Application Data

(60) Provisional application No. 60/666,994, filed on Mar. 31, 2005.

(51) Int. Cl.
*C12N 5/00* (2006.01)
(52) U.S. Cl. ...................................................... 435/377
(58) Field of Classification Search ........................ None
See application file for complete search history.

(56) References Cited

U.S. PATENT DOCUMENTS

| | | | |
|---|---|---|---|
| 5,843,780 | A | 12/1998 | Thomson |
| 6,610,541 | B2 | 8/2003 | Alnemri |
| 6,689,784 | B2 | 2/2004 | Bebbington et al. |
| 6,747,050 | B1 | 6/2004 | Kim et al. |
| 6,800,619 | B2 | 10/2004 | Charrier et al. |
| 2006/0003446 | A1* | 1/2006 | Keller et al. ............... 435/366 |
| 2009/0170198 | A1 | 7/2009 | Rezania |

OTHER PUBLICATIONS

Tada S et al. 2005. Characterization of mesendoderm: a diverging point of the definitive endoderm and mesoderm in embryonic stem cell differentiation culture. Development 132: 4363-4374.*
Technau U et al. 2003. Origin and evolution of endoderm and mesoderm. Int J Dev Biol 47: 531-539.*
Rodaway A et al. 2001. Mesendoderm: an ancient germ layer? Cell 105: 169-172.*
"Caspases." from the Sigma-Aldrich online technical library. <url:// www.sigmaaldrich.com/sigma/rbi-handbook/sg_ls_cs_rbibook_ caspase.pdf>, accessed online Sep. 5, 2008.*
Barthelery M et al. 2007. Nuclear proteomics and directed differentiation of embryonic stem cells. Stem Cells Dev 16(6):905-19.*
Gadue, P., et al., "Wnt and TFG-signaling are required for the induction of an in vitro model of primitive streak formation using embryonic . . . ," PNAS 103:16806-16811 (2006).
Gardiner, M.R., et al., "Zebrafish KLF4 is Essential for Anterior Mesododerm/Pre-Polster Differentiation and Hatching," Devo Dynam 234:992-996 (2005).
Glinka, A., et al., "Dickkopf-1 is a member of a new family of secreted proteins and functions in head induction," Nature 391:357-362 (1998).
Krupnik, V.E., et al., "Function and structural diversity of the human Dickkopf gene family," Gene 238:301-313 (1999).
Mao, B., et al., "Kremen2 modulates Dickkopf2 activity during Wnt/LRP6 signaling," Gene 302:179-183 (2003).
Patient, R.K., et al, "The GATA family (vertebrates and invertebrates)," Curr Opin Gen Devo 12:416-422 (2002).
Wu, W., et al., "Mutual antagonism between dickkopf1 and dickkopf2 regulates Wnt/beta-catenin signalling," Curr Biol 10:1611-1614 (2000).
Lugus, J.J. et al., "Developmental Relationship Between Hematopoietic and Endothelial Cells" Immunol. Res. 2005, 32: 57-74.
Niwa, H. et al., "Quantitative expression of Oct-3/4 defines differentiation, dedifferentiation or self-renewal of ES cells" Nature Gen. 2000, 24:372-376.
R&D Systems Inc., Caspase Inhibitor, Sample Pack, Catalog No. FMKSP01 (2000).
Kidd, Proteolytic Activities That Mediate Apoptosis, Annu. Rev. Physiol. (1998) 60:533-73.
Aravind, L., et al., "Apoptotic Molecular Machinery: Vastly Increased Complexity in Vertebrates Revealed by Genome Comparisons," Science 291:1279-1284 (2001).
Chambers, I., et al., "Functional Expression Cloning of Nanog, a Pluripotency Sustaining Factor in Embryonic Stem Cells," Cell 113:643-655 (2003).
Earnshaw, W.C., et al., "Mammalian Caspases: Structure, Activation, Substrates, and Functions During Apoptosis," Annu. Rev. Biochem. 68:383-424 (1999).
Evans, M.J., et al., "Establishment in Culture of Pluripotential cells From Mouse Embryos," Nature 292:154-156 (1981).
Green, D.R., et al., "Mitochondria and Apoptosis," Science 281:1309-1312 (1998).
Kaufmann, S.H., et al., "Specific proteolytic cleavage of poly(ADP-ribose) polymerase: an early marker of chemotherapy-induced apoptosis," Cancer Res. 53:3976-3985 (1993).
Kidd, V.J., "Proteolytic Activities that mediate Apoptosis," Annu. Rev. Physiol. 60:533-573 (1998).
Lazebnik, Y.A., et al., "Cleavage of poly(ADP-ribose) polymerase by a proteinase with properties like ICE," Nature 371:346-347 (1994).
Martin, G.R., "Isolation of a pluripotent cell line from early mouse embryos cultured in medium conditioned . . . ," Proc. Natl. Acad. Sci USA 78:7634-7638 (1981).
Nicholas, J., et al., "Formation of Pluripotent Stem Cells in the Mammalian Embryo Depends on the POU Transcription Factor Oct4," Cell 95:379-391 (1998).
Srinivasula, S.M., et al., "Generation of Constitutively Active Recombinant Caspases-3 and-6 by Rearrangement of Their Subunits," Journal of Biological Chemistry 273:10107-10111 (1998).
Thomson, J.A., et al., "Embryonic Stem Cell Lines Derived from Human Blastocysts," Science 282:1145-1147 (1998).
Thornberry, N.A., et al., "Caspases: Enemies Within," Science 281:1312-1316 (1998).

* cited by examiner

*Primary Examiner* — Lora E Barnhart
(74) *Attorney, Agent, or Firm* — Quarles & Brady LLP; Sara D. Vinarov

(57) ABSTRACT

The invention relates to a method to induce primate embryonic stem cells to differentiate into a relatively homogenous population of mesendoderm cells by treatment with caspase-like inhibitors. Also described is a population of mesendoderm cells obtained therefrom. The embryonic stem cell derived mesendoderm cells have the general morphological and cell surface marker characteristics of mesendoderm cells.

12 Claims, 7 Drawing Sheets

DIFFERENTIATION OF PLURIPOTENT EMBRYONIC STEM CELLS

CROSS-REFERENCE TO RELATED APPLICATIONS

This application claims the benefit of U.S. Provisional Application No. 60/666,994 filed Mar. 31, 2005 which is incorporated herewith by reference in its entirety.

STATEMENT REGARDING FEDERALLY SPONSORED RESEARCH OR DEVELOPMENT

This invention was made with United States government support awarded by the following agency: NIH RR000167. The United States has certain rights in this invention.

BACKGROUND OF THE INVENTION

Primate (particularly human) ES cell lines have widespread utility in connection with human developmental biology, drug discovery, drug testing, and transplantation medicine. For example, current knowledge of the post-implantation human embryo is largely based on a limited number of static histological sections. Because of ethical considerations the underlying mechanisms that control pluripotency, differentiation and developmental decisions of the early human embryo remain essentially unexplored.

Recently, however, primate (e.g. monkey and human) pluripotent embryonic stem cells have been derived from preimplantation embryos. See, for example, U.S. Pat. No. 5,843,780 and J. Thomson et al., 282 *Science* 1145-1147 (1998). The disclosure of these publications and of all other publications referred to herein are incorporated by reference as if fully set forth herein. Notwithstanding prolonged culture, these cells stably maintain a developmental potential to form advanced derivatives of all three embryonic germ layers.

It is generally known, however, that stem cells are defined to be cells which are capable both of self-renewal and differentiation into one or more differentiated cell types. Human embryonic stem cells are a category of stem cells created from human pre-implantation blastocysts. Human embryonic stem cells are pluripotent and may be totipotent, meaning that they can certainly differentiate into many cell types evidenced in an adult human body and may be capable of differentiating into all cell types present in the human body.

It is believed that one of the exciting potential uses of stem cells is for human tissue transplantation. It is hoped and expected that techniques can be developed to direct the differentiation of stem cells into specific lineages, which can then be transferred into the human body to replace or enhance tissues of the body. In order to do that, there first needs to be a clear understanding as to how cells become pluripotent in comparison to other cells. Next, techniques must be developed to direct the differentiation of stem cells into the specific cell lineages desired. Techniques have already been proposed to direct stem cell cultures into lineages of hematopoietic, neural, cardiomyocyte, pancreatic and other lineages. These techniques have proven to be quite different from each other and independent in the sense that a new and different technique is required for each new desired lineage.

Unfortunately, it still remains largely unknown why some cells become pluripotent and others do not. It is generally understood that in the early mammalian embryo, cleavage-stage blastomeres and at least some cells of the blastocyst's inner cell mass (ICM) all have the potential to contribute to any cell type of the body (Pedersen, 1986). ES cells, which are derived from early embryonic cells, can be expanded in vitro without limit, and retain the ability to form any cell type of the body (Evans and Kaufman, 1981; Martin, 1981; Thomson et al., 1998). Only a few key factors indicating pluripotency, such as Oct4 (Nichols et al., 1998) and Nanog (Chambers et al., 2003), have been identified so far, and the underlying mechanisms which control and maintain this remarkable state are largely yet unknown.

In contrast to the little that is known in the art about the control of pluripotency, there has been extensive characterization of the pathways controlling programmed cell death over the last three decades (Kerr et al., 1972; Ellis and Horvitz, 1986; Ellis et al., 1991). Programmed cell death and its morphological manifestation, apoptosis, are controlled by a complex, well-characterized genetic program in which mitochondria often have a central role (Ellis et al., 1991). During the course of programmed cell death, the mitochondrial membrane potential, $\Psi\Psi_m$, decreases, and the mitochondria release small proteins, including cytochrome c (Liu et al., 1996) and apoptosis inducing factor (AIF) (Green and Reed, 1998; Joza et al., 2001). This release ultimately results in the activation of some cysteine proteases, or caspases (Thomberry and Lazebnik, 1998). The caspases are divided into a group of initiator caspases (Earnshaw et al., 1999), including caspase-2, -8, -9, and -10, which promote programmed cell death in its early phases, and a group of terminal executioner caspases, including caspase-3, -6, and -7, which cleave several vital proteins, including poly(ADPribosyl) polymerase or PARP-1 (Lazebnik et al., 1994). Proteolysis of PARP-1 and other proteins eventually causes a sequential and controlled breakdown of the cell (Kidd, 1998).

Some studies have suggested that the programmed cell death system emerged concomitantly with the initial evolution of the metazoans (Aravind et al., 2001). Also, metazoans are believed to be the first multicellular animals having various types of cells organized into different types of tissues and organs. Therefore, it is of fundamental importance to understand what causes cells to specialize into different types of cells. While it has been demonstrated that human ES cells will differentiate into many progeny cells types, it has been difficult for researchers to create distinct and uniform cultures of progeny of human ES cells, which can be directed into a particular lineage or lineages. Accordingly, a need exists for the investigation of novel pathways and development of techniques that can be used to stably culture and direct primate embryonic stem cell differentiation into specific cell types as uniformly as practicable.

BRIEF SUMMARY OF THE INVENTION

The present invention is summarized as a method which permits the direct differentiation of a culture of pluripotent embryonic stem cells into a culture of mesendoderm cells. The method includes culturing the pluripotent embryonic stem cells in the presence of at least one caspase-like inhibitor in a culture medium capable of supporting the proliferation and differentiation of embryonic stem cells into mesendoderm cells.

In one aspect the caspase-like inhibitor is a caspase-3 like inhibitor such as DEVD.fmk.

In another aspect the invention provides a culture of mesendoderm cells derived from pluripotent embryonic stem cells, wherein the differentiated cells have reduced caspase-like activity, along with morphology and cell surface markers characteristic of mesendoderm cells.

In this aspect the novel mesendoderm culture is a relatively homogenous population of mesendoderm cells.

In another aspect the invention provides a method of selecting for a cell population enriched for pluripotent cells by assaying a culture of embryonic stem cells for the presence of a protein marker exhibiting caspase-like activity and culturing the cells having caspase-like activity to obtain a population enriched for pluripotent cells.

In another aspect, the invention provides a novel marker having caspase-like activity for use in selecting pluripotent embryonic stem cells.

In yet another aspect, the invention provides a method for maintaining a pluripotent culture of embryonic stem cells by contacting the cells with an effective amount of an agonist of an apoptotic pathway having caspase-like activity to inhibit differentiation of the cells; and exposing the cells to cell growth conditions such that the cells proliferate.

Other objects, advantages and features of the present invention will become apparent from the following specification when taken in conjunction with the accompanying drawings.

DETAILED DESCRIPTION OF THE INVENTION

Figure 1:
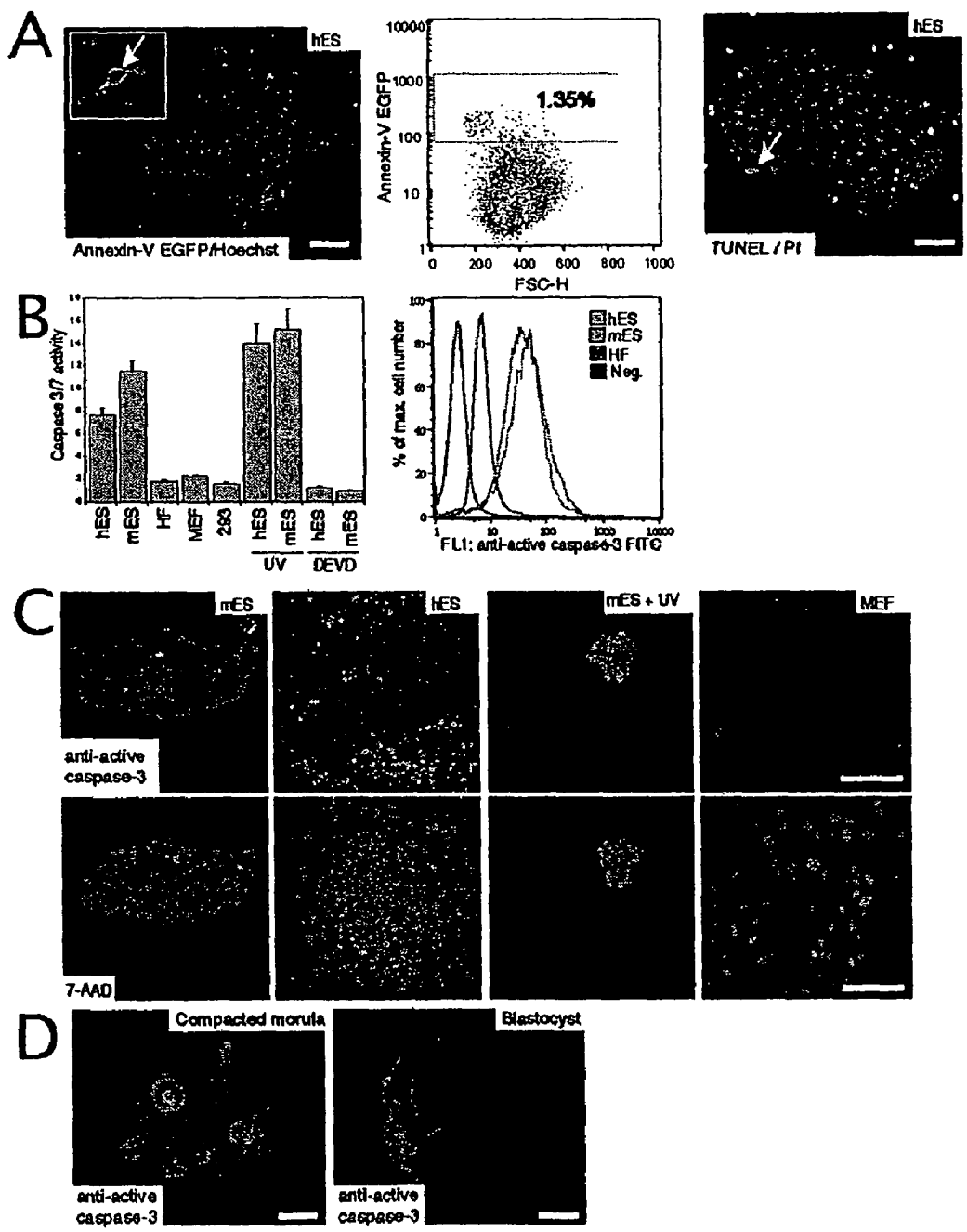
FIGS. 1A-D illustrate elevated caspase-3-like activity in pluripotent cells. (A) In situ staining of a human ES cell colony in standard culture conditions with Annexin-V conjugated to EGFP (left); human ES cells undergoing programmed cell death with traditional features of apoptotic cells, including nuclear condensation, membrane fragmentation, Annexin-V binding, and disintegration into apoptotic bodies (inset, left). Flow cytometry analysis of Annexin-V staining of human ES cells in standard culture conditions (middle). TUNEL assay of human ES cells in standard culture conditions (right), arrows indicate apoptotic cells, bars=25 µm (B) Undifferentiated human and mouse ES cells showed significantly higher levels of caspase-3-like activity than mouse embryonic fibroblasts (MEF), human foreskin fibroblasts (HF), or the human 293T cells in an in vitro caspase-3 assay (left). This activity was increased after exposure to UV light and blocked after caspase-3 blocker treatment (DEVD.fmk). Flow cytometry using an antibody specifically recognizing the activated form of caspase-3 (right) shows that both human and mouse ES cell populations have a significant shift of the entire population in comparison to foreskin fibroblast cells. (C) Staining of human and mouse ES cells, murine fibroblast cells, and UV-light treated mouse ES cells with an antibody specific for activated caspase-3. DNA was stained with propidium iodide (PI), bars=25 µm (D) Staining of pluripotent cells in the pre-implantation mouse embryo with antibody to activated caspase-3, bar=5 µm.

The present invention relates to a method of directing the differentiation of pluripotent primate embryonic stem cells into a homogeneous population of mesendoderm cells, as well as the resultant culture of mesendoderm cells produced therefrom. Applicants have discovered that by blocking caspase-like activity in ES cells, the cells are able to differentiate rapidly (within 2-3 days) into a morphologically uniform population of mesendoderm cells. Accordingly, the method is based on the premise that cultivation of primate embryonic stem cells in the presence of a caspase-like inhibitor causes the cells so treated to differentiate and change their morphology to become mesendoderm cells. In contrast to other techniques for the directed differentiation of embryonic stem cell derived lineages, the novel culture of mesendoderm cells obtained by the method described here appears to form, relatively rapidly, into a uniformly homogenous population of primarily mesendoderm cells having key mesendoderm genes significantly upregulated in comparison to undifferentiated cells.

As used herein the term "mesendoderm cells" refers to the cell population which is a precursor of both mesoderm and endoderm-derived cells. Applicants envision that this novel intermediate cell population obtained through the method of the invention described hereinbelow, would be an ideal precursor, which could be used for producing any of the specialized cells derived from endoderm or mesoderm cells. It is noted that cells and tissues that are derived from endoderm cells include: thymus, thyroid, parathyroid glands, larynx, trachea, lung, urinary bladder, vagina, urethra, gastrointestinal (GI) organs (liver, pancreas), lining of the GI tract, lining of the respiratory tract. Likewise, cells and tissues that are derived from mesoderm cells include: bone marrow (blood), adrenal cortex, lymphatic tissue, skeletal, smooth, and cardiac muscle, connective tissues (including bone, cartilage), urogenital system, heart and blood vessels (vascular system).

Accordingly, in one embodiment, the invention provides a method for making mesendoderm cell cultures which begins with initially culturing undifferentiated primate embryonic stem (ES) cells in a medium under feeder-free conditions. Next, the undifferentiated human ES cells are incubated with a caspase inhibitor, more preferably a caspase-3 inhibitor, and more preferably N-benzyloxycarbonyl-Asp-Glu-Val-Asp fluoromethylketone (DEVD.fmk) to cause the ES cells to rapidly differentiate within 2-3 days into a morphologically uniform population of mesendoderm cells. A caspase inhibitor is an agent which acts to inhibit activity of caspase-3 or to inhibit other caspase-like activity in undifferentiated stem cells to generate mesendoderm cells. This homogenous cell population may be used as an effective intermediate precursor for obtaining specialized endoderm and/or mesoderm cells as described above. It is emphasized that it was not previously known that this medium combined with caspase inhibitors could be used to support the direct differentiation of ES cells into mesendoderm cells. Furthermore, in order to evaluate the effectiveness of the novel method, applicants performed a control where the same volume of DMSO (solvent for DEVD.fmk) was added and no significant effect on the number of undifferentiated cells was observed. It was further observed that a recombinant, constitutively active caspase-3 protein was capable of blocking the effects of DEVD.fmk on both ES cells and embryos. Accordingly, applicants speculate that caspase-3-like activity may be intimately involved in maintaining the pluripotent state by cleavage of chromatin-modifying proteins or transcription factors.

Applicants further envision that other small molecule inhibitors that have been known to block capase activity may be applicable to the methods of the invention, such as for example: polyphenylureas which is a new class of caspase inhibitors believed to act at the BIR2 region of caspase proteins and which are particularly effective in the micromolar range. Another caspase inhibitor that may be applicable to the invention is IDN-5370 which is available through Idun Pharmaceuticals.

Also, a number of peptidic inhibitors have been found by investigators to be useful in blocking specific caspase activity. For example, reversible tetrapeptide inhibitors have been prepared having the structure $CH_3 CO—[P4]-[P3]-[P2]-CH(R) CH_2 CO_2 H$ where P2 to P4 represent an optimal amino acid recognition sequence and R is an aldehyde, nitrile or ketone capable of binding to the caspase cysteine sulfhydryl. Rano and Thomberry, Chem. Biol. 4, 149-155 (1997); Mjalli, et al., Bioorg. Med. Chem. Lett. 3, 2689-2692 (1993); Nicholson et al., Nature 376, 37-43 (1995). Irreversible inhibitors based on the analogous tetrapeptide recognition sequence have been prepared where R is an acyloxymethylketone $—COCH_2 OCOR'$. R' is exemplified by an optionally substituted phenyl such as 2,6-dichlorobenzoyloxy and where R is COCH X where X is a leaving group such as F or Cl. Thomberry et al., Biochemistry 33, 3934 (1994); Dolle et al., J Med. Chem. 37, 563-564 (1994). Likewise, compounds that are useful as caspase inhibitors have also been recently described in U.S. Pat. Nos. 6,800,619 and 6,689,784 (carbamate caspase inhibitors) both assigned to Vertex Pharmaceuticals Incorporated (Cambridge, Mass.) Isoxazoline derivatives have also been used in inhibiting the activity of caspases, as described in U.S. Pat. No. 6,747,050 assigned to LG Chem Investment Ltd. (Seoul, KR). It is also believed that recombinant, active caspases, such as rev-caspases comprising a primary product in which the small subunit is N-terminal to the large subunit can be used for screening and identifying other potential caspase inhibitors applicable to the invention (see, U.S. Pat. No. 6,610,541)

Furthermore, it is believed that while applicants have found that this combination of culture media and caspase inhibitor (DEVD.FMK) is sufficient to support the differentiation of ES cells into mesendoderm cells, it may be possible to use a combination of different caspase-like inhibitors in the culture medium to obtain rapid differentiation. Whether or not a particular caspase-like inhibitor may be useful for causing differentiation can readily be ascertained by empirical experimentation without departing from the concept of the present invention.

What separates this method from prior art derivation of heterogeneous mixtures of cells is the efficiency and relative uniformity of the transition of the cell culture from ES cells to the intermediate precursor, mesendoderm cells. It is noted that in general, other methods have been tried, without success, to achieve this type of uniform transition, such as application of phorbol esters, co-cultivation with stromal cells plus serum, and isolation of endothelial cells from embryoid bodies. None of these efforts reproducibly yielded relatively homogenous cultures of cells. In contrast, applicants have now found a novel approach which is simple, efficient and results in a cell culture of morphologically similar cells having the characteristics of mesendoderm cells as described below.

Figure 3:
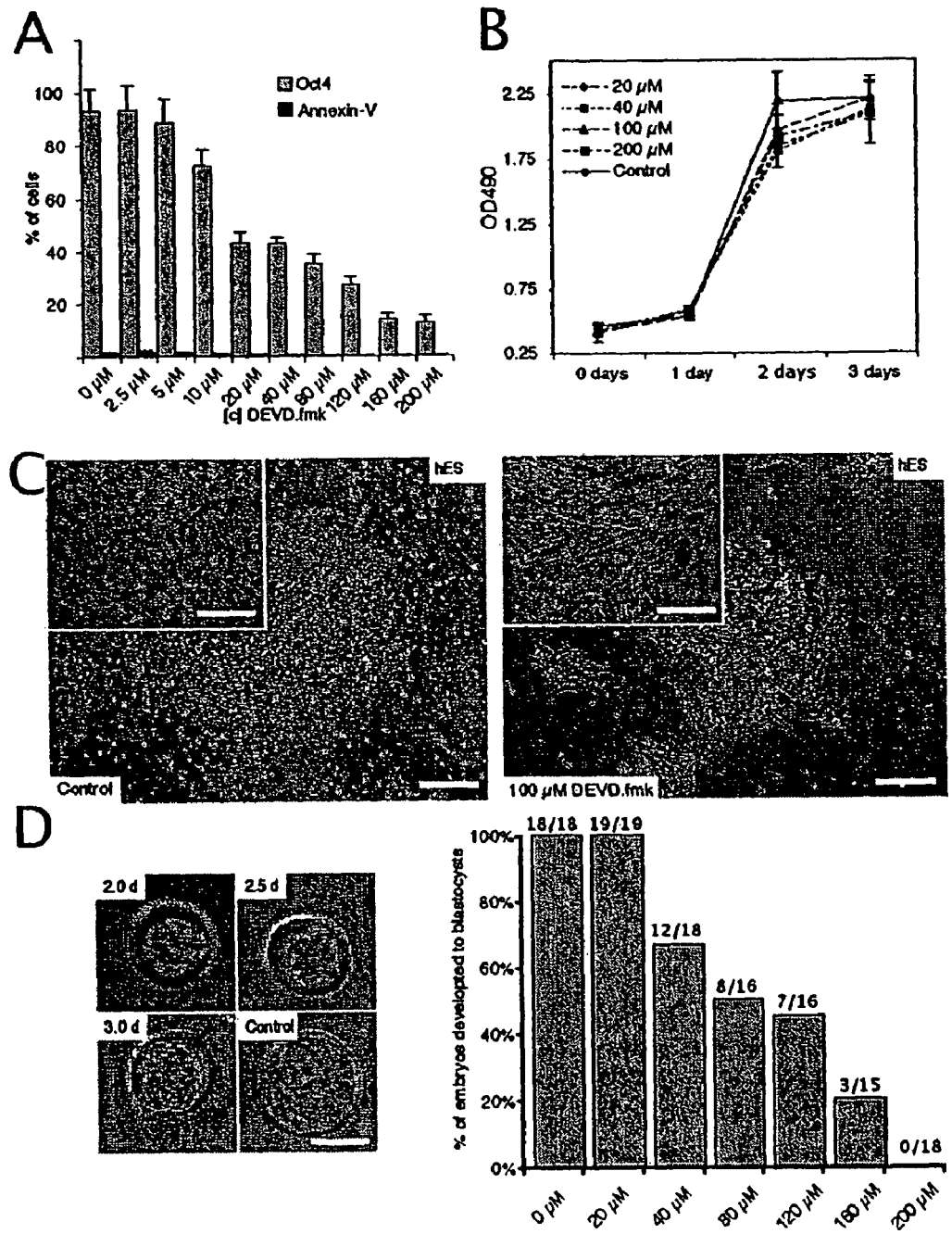
FIGS. 3A-D illustrate blocking caspase-3-like activity causes differentiation. (A) Flow cytometric analysis showing the percentage of Oct4-positive cells and Annexin-V EGFP binding cells after addition of the caspase-3 inhibitor DEVD. fmk at indicated concentrations. DEVD.fmk caused a significant, dose-dependent induction of differentiation in human ES cells and a significant, dose-dependent reduction in Annexin-V binding. (B) Effects of the caspase blocker on proliferation. Application of DEVD.fmk causes a transient decrease in the proliferation rate of ES cells. (C) Application of DEVD.fmk to human ES cells causes differentiation into cells of uniform morphology. Undifferentiated ES cells have a round cellular shape, a high nucleus-to cytoplasm ratio, and several prominent nucleoli. ES cells induced to differentiate with DEVD.fmk have a spindle shaped-morphology with a much smaller nucleus, bar=25 µm. (D) Application of the caspase blocker affects the development of pre-implantation embryos (left). Addition of caspase blocker to uncompacted morula stage (E2.0), early compacted (E2.5) and late compaction stage (E.3.0) embryos resulted in retarded embryos. The number of embryos developing to the fully expanded blastocyst stage is dependent on the dose of DEVD.fmk (right), bar=5 µm.
Figure 4:
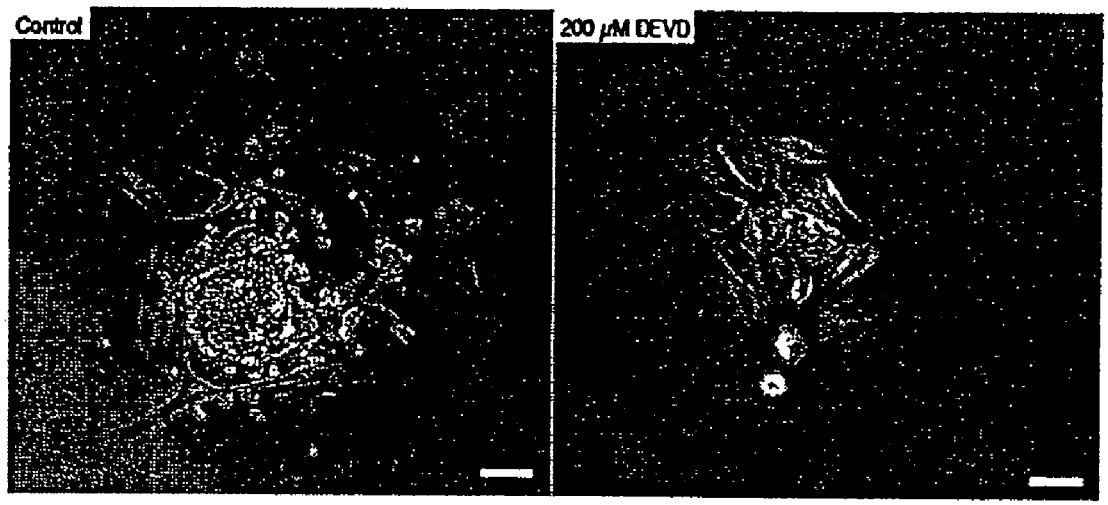
FIG. 4 illustrates the results of embryo culture outgrowth experiments. After 4 days of culture, normal control embryos show outgrowth of trophectoderm cells and a clear and rapid expansion of primitive endoderm cells on top of the trophectoderm cell layer. In contrast, DEVD.fmk-treated embryos show only outgrowth of trophoblast cells, and the formation of a growing epiblast was completely inhibited, bar=5 µm.

In another embodiment, the invention provides a culture of mesendoderm cells produced through the method described herein. The mesendoderm cell culture of the invention has certain characteristics. Applicants have found that ES cells treated with DEVD.fmk differentiated to a spindle shape cell with a much smaller nuclear-cytoplasmic ratio (FIG. 3C, right). Also, these spindle-shaped cells failed to stain for Oct4 by immunocytochemistry (data not shown) indicating loss of pluripotency. DEVD.fmk-treated embryos showed only outgrowth of trophoblast cells, and the formation of a growing epiblast was completely inhibited (FIG. 4). Applicants also found that ES cells which had differentiated into mesendoderm cells also exhibited reduced Annexin-V binding, a marker of early apoptosis in mammalian cells. Other characteristics that applicants have identified in mesendoderm cells have included polarized mitochondria, reduced cytoplasmatic cytochrome c, inhibited caspase-3-like activity, and reduced PARP-1 cleavage (PARP-1 is a target of caspase-3 cleavage). These factors are particularly significant because depolarized mitochondria, cytoplasmatic cytochrome c, caspase-3-like activity, and PARP-1 cleavage are all well-recognized hallmarks of programmed cell death and appear to also be characteristic of viable human and mouse pluripotent cells.

Furthermore, a microarray gene expression analysis was performed and the results showed that many key mesoderm genes were significantly upregulated including at least one gene (DKK4) which has been associated with a common mesoderm and endoderm precursor (mesendoderm). It was found that several other mesendoderm genes were upregulated by several fold in comparison with undifferentiated ES cells. The observed upregulated genes include but are not limited to: brachyury variant A: 73 X; BMP4: 45 X; GATA-3: 9X; WNT5A 5X; WNT3: 3X and DKK4: 137X). It is noted that one feature of the culture of the invention is that the cells are capable of differentiating rapidly (within 2-3 days) into a morphologically uniform population of mesendoderm cells. Applicants note that given the limits of present cell culture technology, however, it cannot be said with certainty that the ES derived mesendoderm cell culture is entirely free of other cell types. However, it can be said that cultures of cells produced by the method described here are at least 75%, and more preferably, over 90% mesendoderm cells exhibiting the characteristics described above. Furthermore, since the precursor ES cells can be grown in any number, this makes possible the generation of large numbers of mesendoderm cells for clinical experimentation or treatment. In contrast, ES cells grown in other media appear to differentiate into a heterogeneous population of cell types with no distinct mesendoderm-appearing cells, which makes it extremely difficult to perform any type of clinical experimentation or treatment.

In another embodiment, the invention provides a method of selecting for a cell population enriched for pluripotent cells, the method essentially entails assaying a culture of embryonic stem cells for the presence of a protein marker exhibiting caspase-like activity. Preferably the protein marker exhibits elevated caspase-3 like activity as compared to cells which have differentiated into for example, mesendoderm cells. This embodiment also provides for a protein marker to facilitate selection of pluripotent cells, wherein the pluripotent cell marker may be a native or recombinant protein which exhibits elevated caspase-like activity. It is also encompassed that cleaved PARP-1 and cleaved p85 fragment of PARP-1 may be used as protein markers for use in selecting a population of pluripotent cells. For example, PARP as described herein may be detected through conventional immunostaining techniques using antibodies that allow detection of the p85 fragment of PARP-1, such as anti-p85 PARP (rabbit polyclonal IgG, available through Promega Corp.) Applicants also envision that these types of novel markers may be relevant for detecting or monitoring the level of differentiation of not only pluripotent cells but also multipotent cells, such as adult stem cells.

In another embodiment, the invention provides a method for maintaining embryonic stem cells in a pluripotent culture by contacting the cells with an amount of an agonist of a apoptotic pathway effective to inhibit differentiation of the cell; and exposing the cells to cell growth conditions such that the cell proliferates. It is encompassed that the agonist would be able to exhibit caspase-like activity and is preferably, caspase-3. Applicants have also found that there is a strong correlation between elevated caspase-3-like activity and cleavage of the classical caspase-3 target PARP-1 into p85 fragment of PARP-1. It is notable that applicants have also found that protein transduction of ES cells with constitutively active caspases, such as recombinant TAT-casp3rev was able to increase the percentage of undifferentiated cells significantly under conditions that usually promote differentiation. Therefore, in accordance with the invention, preferred caspases are mammalian caspases, including any of human caspases 1-10, especially constitutively active caspases such as reverse caspases (e.g., TAT-casp3rev). Other suitable caspases that may be employed by the invention, also include proapoptotic constitutively active caspases.

The following examples are provided as further non-limiting illustrations of particular embodiments of the invention.

EXAMPLES

Material and Methods
Cell Culture.

H1 human ES cells (WiCell) were cultured as previously described and incorporated by reference herein (Amit et al., 2000). Human ES cells were cultured under feeder-free conditions on culture flasks that were pre-coated with matrigel™ (Becton Dickinson Labware, Bedford, MA), using medium conditioned overnight on dense murine embryonic fibroblasts (MEFs) (Xu et al., 2001a). D3 mouse ES cells (ATCC) were cultured under feeder-free conditions in mouse ES cell medium, consisting of 85% Knock-Out DMEM supplemented with 15% Gibco KNOCKOUT Serum Replacement, 2.5 mM glutamine, 0.1 mM beta-mercaptoethanol (Sigma), and 1000 U/l LIF (Esgro) on gelatin-coated plates. Murine and human fibroblasts and the 293T cell lines were cultivated in DMEM +10% Fetal bovine serum (FBS) and 1% non essential amino acids.

Cell Proliferation Assay.

Human ES cells were grown for the indicated time in 96-wells on Matrigel and a MTS test (CellTiter 96, Promega) was performed according to manufacturers' instructions.

Collection of Murine Preimplantation Embryos.

Three to nine-week-old female $B_6C_3F_1$ mice (Charles Rivers) were superovulated with a single 10 IU intraperitoneal injection of Pregnant Mare's Serum Gonadotrophin (Gestyl, Diosynth B.V.—OSS). Forty-eight hours later, ovulation was triggered with a single 10 IU intraperitoneal injection of human Chorionic Gonadotrophin (hCG, Novarel/Ferring) and the female mice were mated with male BDF1 mice (Charles Rivers) of proven fertility. Two-cell stage embryos were flushed from the oviducts of the female mice 38 to 40 hours after the hCG injection using modified-Human Tubal Fluid medium (m-HTF, Irvine Scientific) supplemented with 0.5 mg/mL polyvinyl alcohol (PVA, Sigma). The resulting embryos were washed and cultured in the same medium. Groups of 10-15 embryos were cultured at 37° C. with 5% $CO_2$/95% air in 50 µL drops of m-HTF medium covered with mineral oil (Ovoil, Vitrolife). In the outgrowth experiments, the zona pellucida was digested with pronase and embryos were plated out on gelatin in ES cell derivation medium with 1000 U/mL LIF.

Detection of Apoptotic Cells.

Apoptotic cells were detected using the Annexin-V binding kit (ApoAlert, Clontech) or the TUNEL assay kit (DeadEnd, Promega). PARP activity was determined according to a protocol published by Bakondi and others (Bakondi et al., 2002). In order to detect activated caspase-3 or cleaved p85 PARP-1, cells were fixed in CytoFix (BD), permeablized in CytoPerm, and incubated at 1 µg/ml of anti-active caspase-3 antibody (Cellsignalling) or with 1 µg/ml anti-p85 PARP-1 (Promega) overnight at 4° C. The cells were then washed with CytoPern and incubated with secondary anti-rabbit FITC conjugated antibodies (1:200 dilution) for 60 minutes at room temperature. Mouse embryos were fixed in methanol:DMSO (4:1) (Sigma) overnight at 4° C., re-hydrated in 50% methanol, and then incubated with the primary antibodies (anti-p85 PARP-1 or anti-active caspase-3) in PBS with 2% nonfat instant skim milk and 0.5% Triton-X 100 with gentle shaking overnight at 4° C. Embryos were washed 6 times for 5 minutes at room temperature in PBS with 2% nonfat instant skim milk and 0.5% Triton-X 100 with gentle shaking and incubated in the same way with the secondary fluorescent antibody. Cells and embryos were visualized using a confocal laserscan microscope (Leica) or flow cytometry.

Flow Cytometry.

Cells were treated with trypsin/EDTA and washed with PBS (both reagents are available through Invitrogen Corp.) Dead cells were excluded from analysis by forward- and side-scatter gating. Eighteen samples were analyzed using a FACScan (Becton Dickinson) flow cytometer and Cellquest software (Becton Dickinson). A minimum of 50,000 events were acquired for each sample. For Oct4 expression studies cells were stained for Oct4 using monoclonal Oct4 antibody (1 µl/$10^6$ cells, available through Santa Cruz). Cells were analyzed by flow cytometry analysis in a fluorescence activated cell sorter. Irrelevant anti-mouse isotype-matched antibodies were used as controls.

Recombinant Protein.

Since caspases are naturally occurring as zymogens it is necessary to generate constitutively active caspases. A convenient method for producing a constitutively active caspase is described in Srinivasula et al., (1998) J. Biological Chem. 273(17):10107-10111. According to this method caspases designated "reverse caspases" are generated by switching the order of the large and small subunits such that the engineered molecule mimics a structure presented by the processed wild type active molecule. While the foregoing provides a convenient method for producing an active caspase it is provided by way of exemplification and not limitation.

In this example, Caspase-3 reverse was amplified together with the TAT sequence and cloned into pET160-GW (Invitrogen Corp.) Rosetta 2(DE3)pLysS (Novagen, Madison Wis.) cells transformed with pCasp3 Rev or pET160-GW/CAT (Invitrogen Corp., San Diego, Calif.) were selectively grown in 0.4 L LB+50 ng/ml carbenicillin and induced with 1 M IPTG for 1 hour. Cells were lysed by sonication in 4 mls buffer A (100 mM $Na_2H_2PO_4$/10 mM Tris-HCl/8 M urea [pH 8.0]) and centrifuged. The cleared cell lysate was incubated at room temperature for at least one hour with 1.5 mls NiNTA (Qiagen, Valencia, Calif.) and 10 mM imidazole; washed on a PolyPrep Chormatography column (Biorad) with 2 volumes buffer 2 (6 M urea/20 mM TrisHCl [pH 7.9]/500 mM NaCl), 2 volumes buffer 3 (20 mM TrisHCl [pH 7.9]/150 mM NaCl); and eluted with 5 0.5 ml volumes of buffer 4 (20 mM TrisHCl/ 150 mM NaCl/250 mM imidazol). The highest protein concentration elutions, determined by BCA assay (Pierce, Rockford, Ill.) and visualized on an SDS-PAGE gel with Lumio Green Detection Kit (Invitrogen, San Diego, Calif.), were filter-sterilized through a 0.2 µM filter and used in tissue culture.

Western Blotting Protocol.

Cell lysates were collected from H1 Human ES cells grown on mouse embryonic fibroblasts, D3 Mouse ES cells, Human Foreskin Fibroblasts (HF), 19 MEFs, and apoptotic MEFs induced with 25 µl/ml of 3% $H_2O_2$. Cytosolic and mitochondrial lysates were isolated using the ApoAlert Cell Fractionation Kit (Clontech, Palo Alto, Calif.) and whole-cell lysates were isolated using M-PER Mammalian Protein Extraction Reagent (Pierce, Rockford, Ill.) with 1:1000 dilution of Protease Inhibitor Cocktail (Sigma) and Pefablock SC (final concentration 0.2 µg/ml)(Sigma). Lysates were run on SDS-PAGE gels, transferred to Trans-Blot Transfer Medium (Bio-Rad, Hercules, Calif.) and peroxidase-conjugated secondary antibodies were detected using Supersignal West Pico Chemiluminscent Substrate (Pierce). Cytochrome C was detected with 1:100 dilution of Cytochrome C Antibody (Clontech) and 1:2000 Goat Anti-Rabbit IgG (H+L) (Caltag Laboratories, Burlingame, Calif). COX4 was detected with dilutions of 1:1000 COX4 Antibody (Clontech) and 1:1000 Anti-mouse IgG (g)-Peroxidase (Roche, Basel, Switzerland). PARP was detected with dilutions of 1:400 anti-p85 PARP (rabbit polyclonal IgG) (Promega) and 1:5000 goat Anti-Rabbit IgG (H+L) (Caltag Laboratories).

Cell and Embryo Treatment With Caspase-3 Blocker and Recombinant Caspase-3 Reverse Protein.

Figure 2:
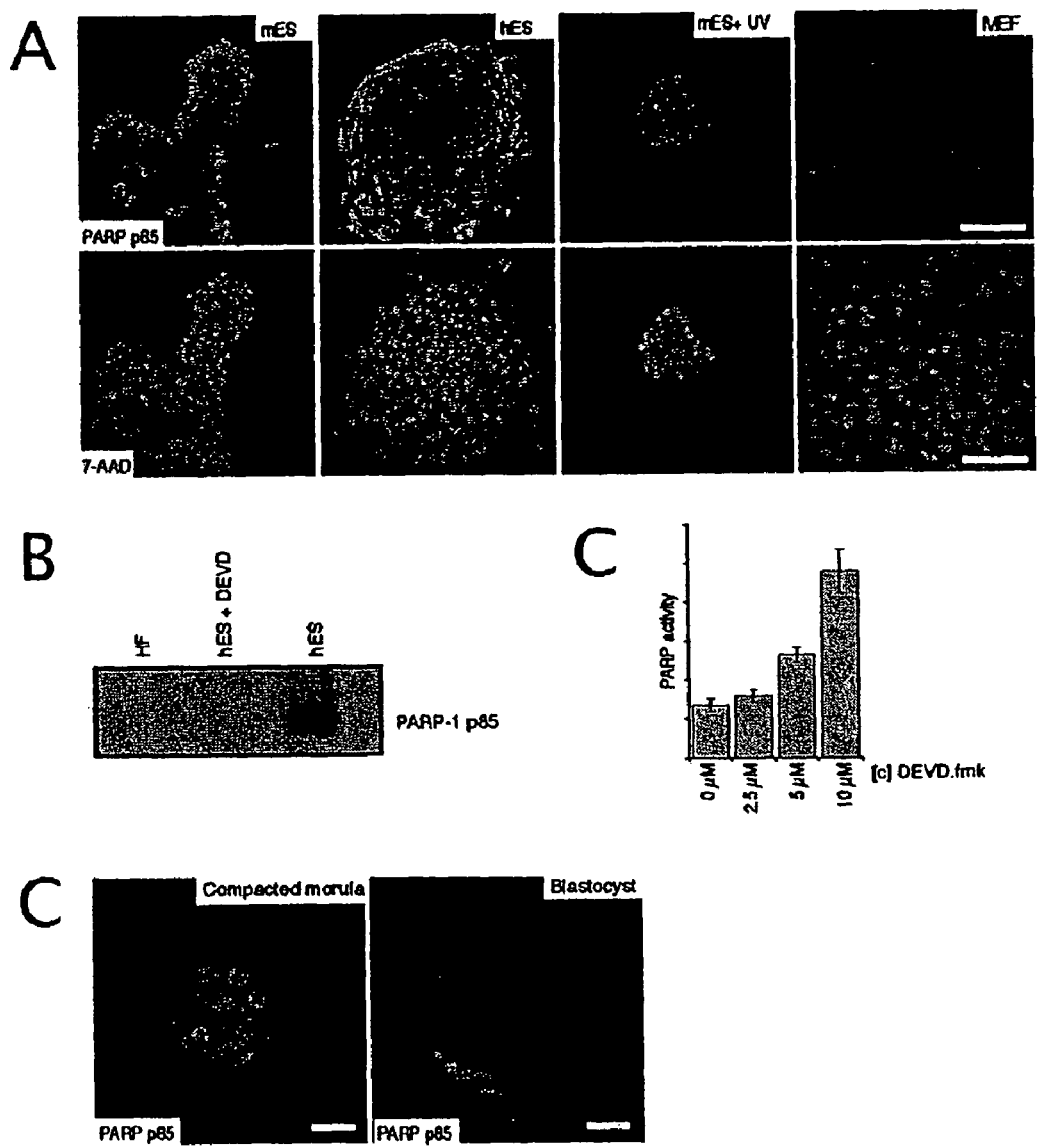
FIGS. 2A-D illustrate PARP-1 is cleaved in pluripotent cells. (A) Staining of mouse and human ES cells with antibodies specific to the cleaved form of PARP-1 (p85). Both are positive for p85, and there is no staining in primary mouse embryonic fibroblasts (MEF). UV-light treated mouse ES cells have increased staining for p85 PARP-1, bar=25 µm. (B) Western immunoblotting with antibodies detection of the cleaved p85 PARP-1 fragment. Significant amounts of p85 PARP-1 in lysates of human ES cells could be detected, whereas in human foreskin fibroblasts as well as in DEVD. fmk treated human ES cells, applicants could not detect p85 PARP-1. (C) In vitro PARP activity assay reveals increasing PARP activity with increasing concentrations of DEVD.fmk. (D) Staining of pre-implantation mouse embryos with antibody specific to the PARP-1 p85 fragment. p85 can be detected in both morula stage blastomeres and in the ICM of the blastocyst (bar=5 µm)

Human ES cells were plated out as small colonies on matrigel, mouse ES cells on gelatin. On the next day ES cells were incubated with the various concentrations of DEVD.fmk as shown in FIG. 2C. DEVD.fmk was added twice a day and half of the ES cell medium was changed daily. As a control, the same volume of DEVD.fmk solvent (DMSO) was added and no significant effect on the number of undifferentiated cells was observed. Recombinant TAT-caspase-3rev was added 4 hours after application of caspase blocker and equal volumes of TAT protein served as controls. Mouse embryos were treated once in the 50 µl microdrop with the given concentration of DEVD.fmk or post-incubation 4 hours later with recombinant TAT-caspase-3rev.

Mitochondrial Membrane Potential.

For in-situ microscopy cells were exposed to 100 nM JC-1 for 45 minutes at 37° C. in 5% $CO_2$, washed twice in medium, and visualized at 490 nm and 585 nm with the confocal laserscan microscope. For flow cytometry, cells were trypsinized and resuspended in cell culture medium together with 100 nM JC-1 and incubated for 45 minutes at 37° C. in 5% $CO_2$, washed twice with regular cell culture medium, and subjected to flow cytometric analysis. Embryos were cultured as described and incubated for 45 minutes at 37° C. in 5% $CO_2$, washed in embryo medium and analyzed with the confocal laserscan microscope.

Results

Caspase-3-Like Activity is Elevated in Pluripotent Cells.

To ensure that the majority of ES cells cultured under standard conditions are not undergoing programmed cell death, applicants determined the extent of spontaneous cell death in standard ES cell cultures. Applicants analyzed ES cells for Annexin-V binding, a marker of early apoptosis in mammalian cells, and for DNA fragmentation. Only a small percentage of human ES cells in standard culture conditions stained in situ with Annexin-V conjugated to enhanced green fluorescent protein (EGFP) (FIG. 1A, left). Rare human ES cells undergoing programmed cell death demonstrated all the traditional features of apoptotic cells, including nuclear condensation, membrane fragmentation, Annexin-V binding and disintegration into apoptotic bodies (FIG. 1A, insert). Flow cytometry revealed that less than 2% of the cells were Annexin-V EGFP-positive (FIG. 1A, middle). Because of damage associated with dissociation, 2% is likely an overestimate of the number of apoptotic cells in intact colonies. Similar results were obtained in experiments using mouse ES cells (data not shown). Genomic DNA from undifferentiated human (FIG. 1A, right) and mouse (data not shown) ES cell lines stained positive in only very few cells in TUNEL assays.

Activation of caspase-3 is widely considered a marker of the late stages of programmed cell death. In vivo, most of the caspase-3-like enzymatic activity is attributed to caspase-3 and -7. Applicants have therefore assayed caspase-3-like activity in undifferentiated human and mouse ES cell lines using an in vitro cell lysate assay (FIG. 1B, left). Unexpectedly, undifferentiated human and mouse ES cells showed significantly higher levels of caspase-3-like activity than did mouse embryonic fibroblasts, human foreskin fibroblasts and the human kidney-tumor cell line 293T (t-test, one-tailed distribution, unequal variance; human ES cells: $p<0.01$, mouse ES cells $p<0.01$). The caspase-3-specific blocking peptide derivative DEVD.fmk reduced this activity and exposure to ultraviolet (UV) light increased this activity in ES cells (FIG. 1B). To further characterize the elevation of caspase-3-like activity in individual ES cells, applicants performed flow cytometry using an antibody specifically recognizing the activated form of caspase-3 (FIG. 1B, right). Both human and mouse ES cell populations showed a significant shift (Chi$^2$-test; for human ES cells T=167.28 for mouse ES cells T=148.77) of the entire population in comparison to foreskin fibroblast cells, demonstrating that the elevated caspase activity was not due to a subpopulation of dying cells. In ES cells, staining for activated caspase-3 was concentrated in the nucleus, with reduced staining in the cytosol (FIG. 1C). In intact embryos, moderate immunostaining of activated caspase-3 was present in all cells of the compacted morula, and in the ICM, but was largely absent in the trophectoderm (FIG. 1D).

PARP-1 is Cleaved in Pluripotent Cells.

Applicants next assayed whether the caspase-3-like activity led to cleavage of the classical caspase-3 target PARP-1. Applicants observed strong immunostaining to the cleaved p85 fragment of PARP-1 in mouse and human ES cells, but not in primary mouse embryonic fibroblasts (FIG. 2A). UV light-treatment of mouse ES cells mildly increased staining for p85 PARP-1. Western immunoblotting with antibodies that allow detection of the p85 fragment of PARP-1 (FIG. 2B), detected significant amounts of cleaved PARP-1 in lysates of human ES cells but not in foreskin fibroblast cells. Treatment of human ES cells with a caspase-3blocker, DEVD.fmk, caused the disappearance of the p85 PARP-1 fragment in Western blot analysis, and caused the upregulated PARP-1 activity (t-test, one-tailed distribution, unequal variance; $p<0.01$)(FIG. 2C). The antibody specific to the PARP-1 p85 fragment stained both cells of the mouse morula and ICM, but not trophectoderm of the blastocyst (FIG. 2D), a staining pattern similar to the pattern of active caspase-3.

Blocking Caspase-3-Like Activity Causes Pluripotent Cells to Differentiate.

To analyze the biological significance of caspase-3-like activity for self-renewal in ES cells, applicants have performed loss of function experiments. Addition of the caspase-3 inhibitor DEVD.fmk caused a significant (t-test, one-tailed distribution, unequal variance; $p<0.01$), dose dependent induction of differentiation in human ES cells (FIG. 3A) as measured by Oct4 staining, and a significant (t-test, one-tailed distribution, unequal variance; $p=0.0011$), dose-dependent reduction in the rate of programmed cell death as measured by Annexin-V EGFP staining. Similar effects were observed with mouse ES cells (data not shown). For the first 48 hours after application of DEVD.fmk, there was a small decrease in proliferation of human ES cells, which was no longer observed after 3 days (FIG. 3B). In contrast to undifferentiated human ES cells (FIG. 3C, left), which have a round shape, a high nuclear-cytoplasmic ratio, and several prominent nucleoli, ES cells treated with DEVD.fmk differentiated to a spindle shape cell with a much smaller nuclear-cytoplasmic ratio (FIG. 3C, right). These spindle-shaped cells failed to stain for Oct4 by immunocytochemistry (data not shown) indicating loss of pluripotency.

The caspase blocker DEVD.fmk inhibited the development of blastocysts when added to uncompacted (E2.0), early compacted (E2.5) and late compacted (E.3.0) mouse morulas in a dose-dependent manner (FIG. 3D), with 200 µM DEVD.fmk treatment completely inhibiting development to expanded blastocysts. DEVD.fmk-treated embryos (n=34) could attach to the culture dish, but always failed to produce prominent rind and core structures characteristic of extraembryonic endoderm overlying epiblast. Instead, they produced only a flattened epithelium morphologically consistent with trophectoderm (FIG. 4).

Constitutively Active Caspase-3 can Block the Effects of DEVD.fmk on Pluripotent Cells.

Figure 5:
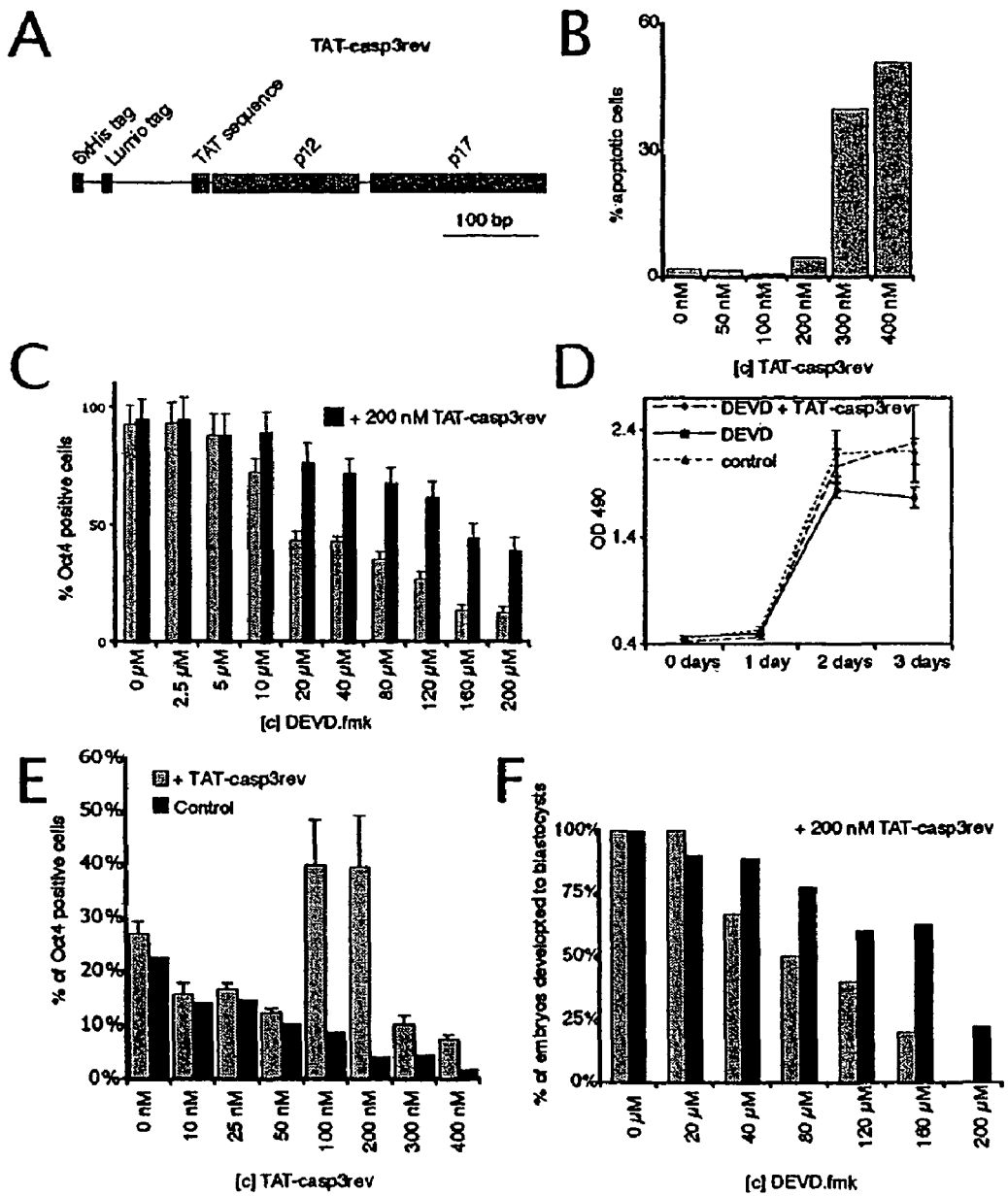
FIGS. 5A-F illustrate that recombinant constitutively active caspase-3 can rescue caspase blockage in pluripotent cells. (A) Schematic diagram of the TAT-casp3rev construct. (B) Protein transduction of human ES cells with TAT-casp3rev causes a dose-dependent increase in cells binding Annexin-V. (C) Protein transduction with recombinant TAT-casp3rev significantly abolishes the differentiation effects of DEVD.fmk. (D) Protein transduction of human ES cells with TAT-casp3rev also increases the proliferation rate of DEVD. fmk treated cells. (E) Protein transduction of ES cells with TAT-casp3rev increases the percentage of undifferentiated cells significantly under conditions that usually promote differentiation. (F) TAT-casp3rev increases the number of DEVD.fmk-treated embryos that reach the expanded blastocyst stage.
Figure 6:
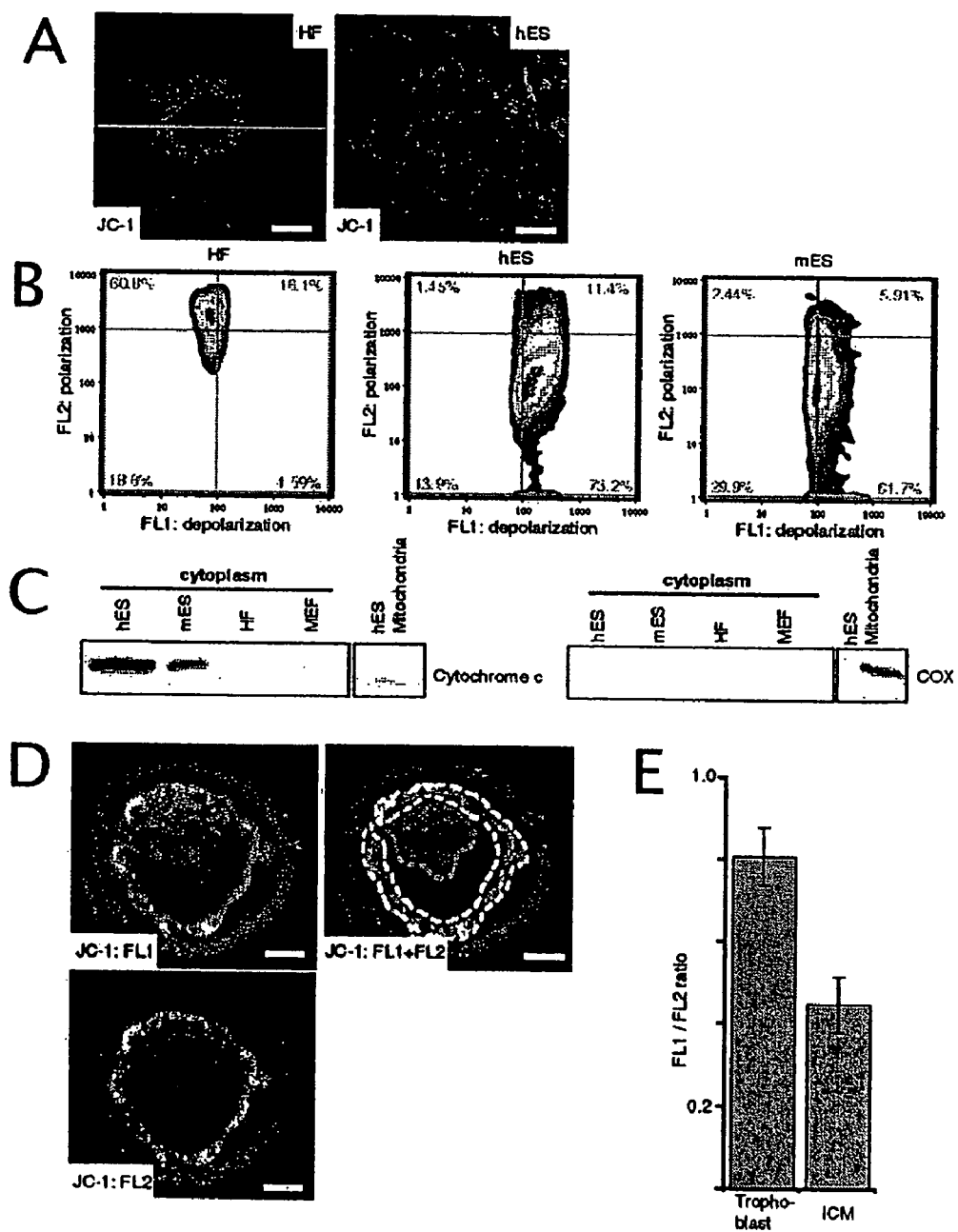
FIGS. 6A-E show that mitochondria in pluripotent cells are partially depolarized, and cytochrome c can be found in the cytoplasm. (A) Fluorescence microscopy of primary human foreskin fibroblasts stained with JC-1 revealed that the majority of mitochondria were red fluorescent, indicating their polarization (left), whereas human ES cells stained with JC-1 were mainly green, indicating significant depolarization of their mitochondria (right), bar=5 µm. (B) Assay of JC-1 staining determined by flow cytometry. The majority of mitochondria in control fibroblasts are polarized, (FL1− FL2+) whereas the majority of mitochondria in ES cells were depolarized (FL1+ FL2−). (C) Western immunoblotting of the cytoplasmic fractions shows significant amounts of cytochrome c in the cytoplasm of both mouse and human ES cells. Cytoplasmic fractions of primary human and mouse fibroblasts are negative for cytochrome c. Control experiments with an antibody against cytochrome oxidase IV show that this protein is absent from the cytoplasm of any of these cells. (D) Staining of fully expanded mouse blastocysts with the JC-1 dye and analysis with confocal laserscan microscopy reveal that the ICM demonstrates a mitochondrial shift towards green fluorescence (FL1), bar=10 µm. (E) Analysis of the red/green fluorescence ratio in the ICM and in the trophoblast cells of 8 different blastocysts shows a significantly lower red/green (FL2/FL1) ratio in the ICM than in the trophectoderm.

To demonstrate that the DEVD.fmk effects were specifically due to the inhibition of caspase-3-like activity, applicants also performed gain of function experiments using protein transduction of a recombinant, constitutively active caspase-3 (FIG. 5A) to see if applicants could overcome the effects of DEVD.fmk. This recombinant caspase-3 (casp3rev), which does not require activation by other caspases (Srinivasula et al., 1998), was fused to the human immunodeficiency virus (HIV) transactivating regulatory protein (TAT) transduction domain, overexpressed in *E. coli*, purified, and used to transduce ES cells (Vocero-Akbani et al., 1999). Applicants found that this recombinant caspase protein was rapidly taken up by ES cells with an increase of caspase-3-like activity (data not shown), and at higher doses, resulted in an increase in the number of apoptotic ES cells in culture (FIG. 5B). At a concentration of 200 nM, TAT-casp3rev minimally affected the apoptosis rate (FIG. 5B), but was able to significantly reduce the differentiation-inducing effects of DEVD.fmk (t-test, one-tailed distribution, equal variance; $p<0.01$) (FIG. 5C). Transduction with TAT-casp3rev also increased the proliferation rate of DEVD.fmk-treated ES cells significantly (t-test, one-tailed distribution, unequal variance; p=000122) (FIG. 5D).

To further test the involvement of caspase-3-like activity in the self-renewal of ES cells, applicants transduced human ES cells with TAT-casp3rev in cell culture medium that does not support self-renewal, but instead results in differentiation (unconditioned medium in the absence of fibroblasts for human ES cells). In these culture conditions, a significantly higher percentage of human ES cells cultured with 200 nM TAT-casp3rev remained Oct4 positive after three days of culture (t-test, one-tailed distribution, unequal variance; $p<0.01$) (FIG. 5E).

Applicants also assayed whether transduction with TAT-casp3rev could rescue the development of DEVD.fmk-treated mouse embryos. In contrast to embryos cultured with DEVD.fmk alone, a greater number of embryos cultured with both DEVD.fmk and TAT-casp3rev reached the expanded blastocyst stage (FIG. 5F).

Mitochondria are Partially Depolarized and Cytochrome c is Present in the Cytoplasm of Pluripotent Cells.

Mitochondrial depolarization and cytochrome c release into the cytoplasm are initial steps of some pathways of programmed cell death. Applicants, therefore, measured the membrane potential of mitochondria in ES cells and primary human foreskin fibroblasts using the specific mitochondrial fluorescent carbocyanine (JC)-1 dye. JC-1 accumulates selectively in polarized mitochondria, where it fluoresces red. Upon depolarization, JC-1 loses its affinity for mitochondria and fluoresces green. Thus, the ratio between red and green fluorescence indicates the degree of mitochondrial polarization and is directly influenced by the mitochondrial membrane potential, $\Psi\Psi_m$.

Confocal laserscan microscopy of primary human foreskin fibroblasts stained with JC-1 revealed that the majority of mitochondria were red fluorescent, indicating their polarization (FIG. 4A, left). In contrast, ES cells stained with JC-1 were mainly green, indicating depolarization of their mitochondria (FIG. 4A, right). To determine the polarization status of mitochondria in the entire cell population, applicants assayed JC-1 stained cells by flow cytometry (FIG. 4B). Applicants found that the majority of mitochondria in control fibroblasts were polarized, being positive in the red FL2 channel and negative in the green FL1 channel, whereas the majority of mitochondria in ES cells were depolarized, being positive in the green FL1 channel and negative in the FL2 red channel.

As the ES cell mitochondria were partially depolarized, applicants anticipated there would be significant amounts of cytochrome c in the cytoplasm. Applicants, therefore, isolated cytoplasmic and mitochondrial protein fractions separately. Western immunoblotting of the cytoplasmic fractions (FIG. 4C) revealed significant amounts of cytochrome c in the cytoplasm of both mouse and human ES cells but not in primary human or mouse fibroblasts. Control experiments with an antibody against cytochrome oxidase IV demonstrated that this protein was absent from the cytoplasm of all of these cells, suggesting selective release of cytochrome c rather than global leakage of mitochondrial proteins.

Applicants also addressed whether mitochondrial depolarization occurred in the pluripotent cells of the early mouse embryo by staining fully expanded mouse blastocysts with the JC-1 dye and performing confocal laserscan microscopy (FIG. 4D). Analysis of the red/green fluorescence ratio in 8 different blastocysts showed a significantly ($p<00.01$) lower red/green ratio in the ICM than in the trophectoderm (FIG. 4E). Together, these results indicate that mitochondrial depolarization and the presence in the cytoplasm of cytochrome c are characteristic features of undifferentiated pluripotent cells.

Microarray Analysis of DEVD Treated Cells

Figure 7:
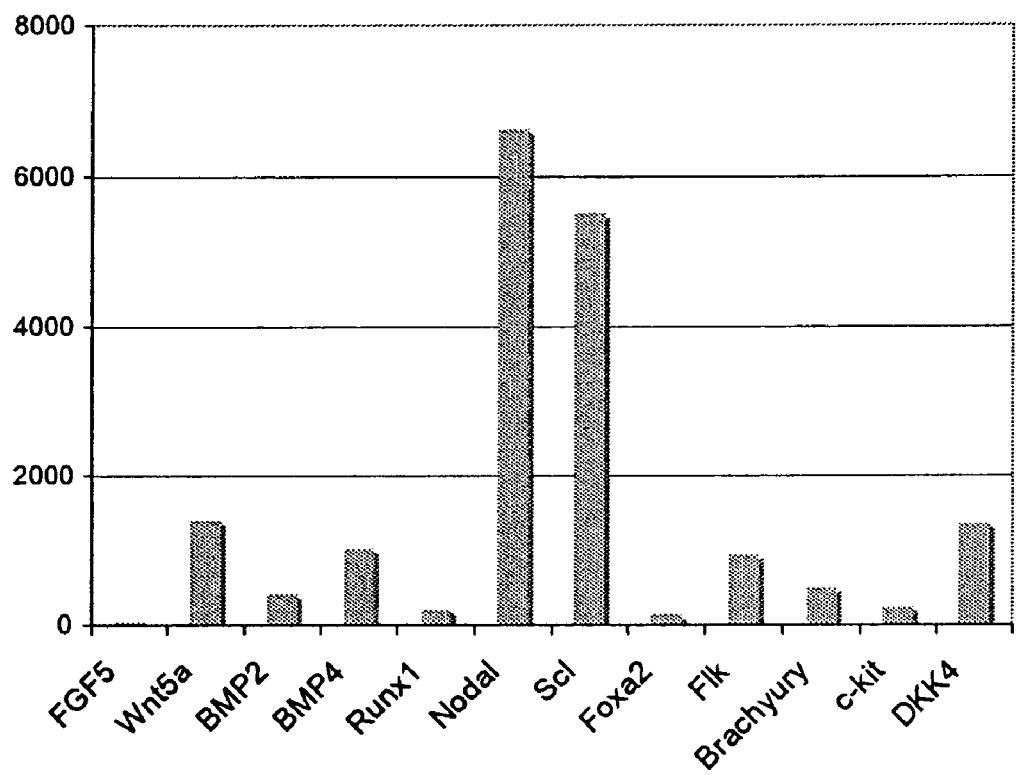
FIG. 7 is a graphical presentation of data from a microarray analysis of DEVD treated human ES cells showing the changes in levels of certain up-regulated genes in those cells.

Since ES cells differentiate relatively uniformly from their undifferentiated state into the spindle-shaped cells, we performed a microarray analysis of the differentiated human cells treated with DEVD.fmk. The results, presented in FIG. 7, revealed mainly mesodermal and endodermal markers. Interestingly, one of the genes showing high up-regulation (over 170-fold) was the human dickkopf homolog DKK4. In both zebrafish and Xenopus, dickkopf genes have been associated with the development of mesoderm and endoderm. The identity of the differentiated cell type is most likely a common precursor of mesoderm and endoderm ("mesendoderm").

Transient Caspase-3 Activity Burst During Differentiation

We determined caspase activity in ES cells after induction of differentiation. In parallel, we monitored the apoptosis rate using an Annexin-V binding assay. During the first 24 hours after induction of differentiation, we did not observe any significant increase in apoptosis rate, but we did detect a significant increase in caspase-3-like activity in whole cell lysate assays. Around 3 to 6 hours after induction of differentiation with retinoic acid, we observed a sharp peak in caspase-3 activity. After approximately 12 to 24 hours, we observed an additional increase in caspase activity, probably due to an increase in apoptosis rate.

Caspase Sensor

We also transfected ES cells with a caspase sensor system. This system contained three components: a nuclear translocation signal, an EYFP fluorescence protein, and a cytoplasmic translocation signal. The latter is separated from the EYFP by the PARP-1 caspase-3 cleavage motif and is much stronger than the nuclear translocation signal. Therefore, in cells with no caspase activity, we expected to observe cytoplasmic localized EYFP activity. As soon as caspases become active in cells, the caspase should cleave off the cytoplasmic signal and the protein should be translocated to the nucleus. Thus the presence of nuclear EYFP is intended to be an indicator of caspase activity. When transfected into NIH 3T3 cells, the caspase sensor system was localized only in the cytoplasm of the transfected cells. Only after induction of programmed cell death, did the EYFP become localized to the nucleus of the cells. However, when the sensor system was transfected into human ES cells, both cytoplasmic and nuclear EYFP activity was detected in all transfected ES cells, indicating a baseline presence of caspase activity. After the cells were induced to differentiate, the localization of the EYFP activity to the nucleus was enhanced, indicating increase caspase activity.

Discussion

Our results suggest a previously unrecognized relationship between the molecular pathways controlling programmed cell death and those controlling self-renewal and differentiation of pluripotent cells. Depolarized mitochondria, cytoplasmic cytochrome c, elevated caspase-3-like activity, and PARP-1 cleavage, all well-recognized hallmarks of programmed cell death, appear to also be characteristic of viable human and mouse pluripotent cells. Our results also indicate that caspase-3-like activity is not just a marker of pluripotent cells, but is essential to the maintenance of both ES cells and the pluripotent cells of the pre-implantation embryo.

Evidence for a pivotal role of caspase-3-like activity in promoting self-renewal in pluripotent cells is demonstrated in our loss of function experiments. Application of the caspase-3-like activity blocker DEVD.fmk caused a rapid, dose-dependent differentiation of ES cells, and dose-dependent developmental arrest of pre-implantation embryos at the late morula stage. Previous work indicates that application of DEVD.fmk does not induce arrest during the transition of 2-8 cell to morula stage embryos (Xu et al., 2001b). This could mean that caspase-3-like activity may be crucial for the establishment or maintenance of the ICM when the first differentiated lineage, the trophectoderm, separates from the pluripotent cells of the embryo. Indeed, the DEVD.fmk-treated embryos developed only into trophoblast-like cells when allowed to attach to the culture dish, a phenotype with striking similarity to Oct4-deficient embryos (Nichols et al., 1998). Caspases may therefore be part of a previously unelucidated signaling pathway that controls the self-renewal and differentiation of pluripotent cells. Studies on amino acid sequence homologies suggest that caspases emerged concomitantly with the evolution of the metazoans (Aravind et al., 2001). Therefore, it may not be surprising that pathways originally believed to be involved in programmed cell death are present in primitive embryonic cells of modern metazoans, and that they act in a broader way and control self-renewal and differentiation.

Protein transduction with recombinant TAT-casp3rev blocked the effects of DEVD.fmk, demonstrating specificity of the inhibitor. Although TAT-casp3rev failed to completely block the effects of DEVD.fmk, this is not surprising, given that there appears to be a critical range of caspase-3 activity, above which apoptosis increases, and below which differentiation occurs. TAT fusion protein transduction is a complex process influenced by many parameters (Vocero-Akbani et al., 1999), and caspase-specific blocking peptides, like DEVD.fmk, have a relatively short half-life in culture, typically only 2-4 hours (Kidd 1998). Transduction with recombinant TAT-casp3rev actually inhibited ES cells from differentiating under conditions that would otherwise cause differentiation. While it is not yet at all clear whether modulation of caspase-3-like activity would be sufficient to sustainably inhibit differentiation in longer-term ES cell cultures, modulation of caspase activity might lead to new methods for culturing ES cells.

Although caspase-3-deficient mice have been generated, none of these mice has shown a phenotype of the pre-implantation embryo, possibly because of functional redundancy within the caspase protein family (Kuida et al., 1996; de Murcia et al., 1997). Because caspase-3-like activity in vivo is primarily due to both caspase-3 and -7, based on our data, applicants would predict that mice deficient in both caspase-3 and caspase-7 would show a phenotype in the pre-implantation embryo. However, a currently unidentified DEVD-type caspase could also be responsible for our results.

Applicants demonstrated functional caspase-3-like activity in ES cells by examining a known cleavage target, PARP-1. PARP activity is widely considered a cellular emergency reaction and has been associated with global chromatin "loosening" and modifications in Drosophila (Tulin and Spradling 2003). PARP-1 protein is specifically cleaved into two parts by caspase-3-like activity (Kaufmann et al., 1993; Casiano et al., 1996): an 85 kDa C-terminal fragment (p85) and a 24 kDa N-terminal fragment (p24) (D'Amours et al., 2001). The p24 moiety, which contains the DNA binding motif, binds irreversibly to DNA and to freshly transcribed RNA and can effectively block transcription (Smulson et al., 1998; Yung and Satoh 2001). The p85 fragment contains neoantigens that can be specifically detected by antibodies, and is typically used as a marker of apoptotic cells. It is, therefore, highly unusual that applicants observed a significant amount of p85 in viable ES cells and in cells of the early pre-implantation embryo. Given the suspected role of PARPs in global chromatin remodeling, it is tempting to speculate that PARP-1, p85, or p24 may have an essential role in pluripotency.

Although it is unclear at present what role, if any, PARP activity and PARP cleavage has in the maintenance of the pluripotent state, its cleavage does suggest that a possible role of caspase-3-like activity in the maintenance of pluripotent cells could be to cleave other chromatin-modifying enzymes or transcription factors. Caspase activity not associated with cell death has also been reported in erythroid precursor cells (De Maria et al., 1999a; De Maria et al., 1999b). In those studies, activation of cell death receptors led to caspase activation, which similar to our results, inhibited differentiation. Also similar to our results, treatment with caspase inhibitors promoted differentiation. It has been proposed that caspases bring about the arrest of erythroid differentiation through the cleavage of GATA-1, a transcription factor that drives erythroid differentiation. It is possible then that caspase activity cleaves transcription factors in pluripotent cells that would otherwise cause differentiation, or that some of their cleavage products actively promote self-renewal. In the future, applicants envision identifying the specific targets of caspase activity in pluripotent cells, and determining the mechanisms by which mitochondrial depolarization, cytochrome c release, and activated caspases fail to drive programmed cell death of pluripotent cells.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Amit M, Carpenter M K, Inokuma M S, Chiu C P, Harris C P, et al., (2000) Clonally derived human embryonic stem cell lines maintain pluripotency and proliferative potential for prolonged periods of culture. Dev Biol 227(2): 271-278.

Aravind L, Dixit V M, Koonin E V (2001) Apoptotic molecular machinery: vastly increased complexity in vertebrates revealed by genome comparisons. Science 291(5507): 1279-1284.

Bakondi E, Bai P, Szabo E E, Hunyadi J, Gergely P, et al., (2002) Detection of poly(ADPribose) polymerase activation in oxidatively stressed cells and tissues using biotinylated NAD substrate. J Histochem Cytochem 50(1): 91-98.

Casiano C A, Martin S J, Green D R, Tan E M (1996) Selective cleavage of nuclear autoantigens during CD95 (Fas/APO-1)-mediated T cell apoptosis. J Exp Med 184(2): 765-770.

Chambers I, Colby D, Robertson M, Nichols J, Lee S, et al., (2003) Functional expression cloning of Nanog, a pluripotency sustaining factor in embryonic stem cells. Cell 113(5): 643-655.

D'Amours D, Sallmann F R, Dixit V M, Poirier G G (2001) Gain-of-function of poly(ADPribose) polymerase-1 upon cleavage by apoptotic proteases: implications for apoptosis. J Cell Sci 114(Pt 20): 3771-3778.

De Maria R, Testa U, Luchetti L, Zeuner A, Stassi G, et al., (1999a) Apoptotic role of Fas/Fas ligand system in the regulation of erythropoiesis. Blood 93(3): 796-803.

De Maria R, Zeuner A, Eramo A, Domenichelli C, Bonci D, et al., (1999b) Negative regulation of erythropoiesis by caspase-mediated cleavage of GATA-1. Nature 401(6752): 489-493.

de Murcia J M, Niedergang C, Trucco C, Ricoul M, Dutrillaux B, et al., (1997) Requirement of poly(ADP-ribose) polymerase in recovery from DNA damage in mice and in cells. Proc Natl Acad Sci USA 94(14): 7303-7307.

Earnshaw W C, Martins L M, Kaufmann S H (1999) Mammalian caspases: structure, activation, substrates, and functions during apoptosis. Annu Rev Biochem 68:383-424.

Ellis H M, Horvitz H R (1986) Genetic control of programmed cell death in the nematode C. elegans. Cell 44(6): 817-829.

Ellis R E, Yuan J Y, Horvitz H R (1991) Mechanisms and functions of cell death. Annu Rev Cell Biol 7: 663-698.

Evans M J, Kaufman M H (1981) Establishment in culture of pluripotential cells from mouse embryos. Nature 292(5819): 154-156.

Green D R, Reed J C (1998) Mitochondria and apoptosis. Science 281(5381): 1309-1312. Joza N, Susin S A, Daugas E, Stanford W L, Cho S K, et al., (2001) Essential role of the mitochondrial apoptosis-inducing factor in programmed cell death. Nature 410(6828): 549-554.

Kaufmann S H, Desnoyers S, Ottaviano Y, Davidson N E, Poirier G G (1993) Specific proteolytic cleavage of poly (ADP-ribose) polymerase: an early marker of chemotherapy-induced apoptosis. Cancer Res 53(17): 3976-3985.

Kerr J F, Wyllie A H, Currie AR (1972) Apoptosis: a basic biological phenomenon with wide-ranging implications in tissue kinetics. Br J Cancer 26(4): 239-257.

Kidd V J (1998) Proteolytic activities that mediate apoptosis. Annu Rev Physiol 60: 533-573.

Kraus W L, Lis J T (2003) PARP goes transcription. Cell 113(6): 677-683.

Kuida K, Zheng T S, Na S, Kuan C, Yang D, et al., (1996) Decreased apoptosis in the brain and premature lethality in CPP32-deficient mice. Nature 384(6607): 368-372.

Lazebnik Y A, Kaufmann S H, Desnoyers S, Poirier G G, Earnshaw W C (1994) Cleavage of poly(ADP-ribose) polymerase by a proteinase with properties like ICE. Nature 371 (6495): 346-347.

Liu X, Kim C N, Yang J, Jemmerson R, Wang X (1996) Induction of apoptotic program in cell-free extracts: requirement for dATP and cytochrome c. Cell 86(1): 147-157.

Martin G R (1981) Isolation of a pluripotent cell line from early mouse embryos cultured in medium conditioned by teratocarcinoma stem cells. Proc Natl Acad Sci USA 78(12): 7634-7638.

Menissier de Murcia J, Ricoul M, Tartier L, Niedergang C, Huber A, et al., (2003) Functional interaction between PARP-1 and PARP-2 in chromosome stability and embryonic development in mouse. Embo J 22(9): 2255-2263.

Nichols J, Zevnik B, Anastassiadis K, Niwa H, Klewe-Nebenius D, et al., (1998) Formation of pluripotent stem cells in the mammalian embryo depends on the POU transcription factor Oct4. Cell 95(3): 379-391.

Pedersen R A (1986) Potency, lineage and allocation in preimplantation mouse embryos. In: Rossant J, Pedersen R A, editors. Experimental approaches to mammalian embryonic development. New York: Cambridge University Press. pp. 3-33.

Smulson M E, Pang D, Jung M, Dimtchev A, Chasovskikh S, et al., (1998) Irreversible binding of poly(ADP)ribose polymerase cleavage product to DNA ends revealed by atomic force microscopy: possible role in apoptosis. Cancer Res 58(16): 3495-3498.

Srinivasula S M, Ahmad M, MacFarlane M, Luo Z, Huang Z, et al., (1998) Generation of constitutively active recombinant caspases-3 and -6 by rearrangement of their subunits. J Biol Chem 273(17): 10107-10111.

Thomson J A, Itskovitz-Eldor J, Shapiro S S, Waknitz M A, Swiergiel J J, et al., (1998) Embryonic stem cell lines derived from human blastocysts. Science 282(5391): 1145-1147.

Thornberry N A, Lazebnik Y (1998) Caspases: enemies within. Science 281(5381): 1312-1316.

Tulin A, Spradling A (2003) Chromatin loosening by poly (ADP)-ribose polymerase (PARP) at Drosophila puff loci. Science 299(5606): 560-562.

Vocero-Akbani A M, Heyden N V, Lissy N A, Ratner L, Dowdy SF (1999) Killing HIV infected cells by transduction with an HIV protease-activated caspase-3 protein. Nat Med 5(1): 29-33.

Xu C, Inokuma M S, Denham J, Golds K, Kundu P, et al., (2001a) Feeder-free growth of undifferentiated human embryonic stem cells. Nat Biotechnol 19(10): 971-974.

Xu J, Cheung T, Chan S T, Ho P, Yeung W S (2001b) The incidence of cytoplasmic fragmentation in mouse embryos in vitro is not affected by inhibition of caspase activity. Fertil Steril 75(5): 986-991.

Yung T M, Satoh M S (2001) Functional competition between poly(ADP-ribose) polymerase and its 24-kDa apoptotic fragment in DNA repair and transcription. J Biol Chem 276(14): 11279-11286.

We claim:

1. A method for directing the differentiation of human embryonic stem cells into a population of multipotent cells comprising the steps of
    culturing a population of human embryonic stem cells for 2 to 3 days in a culture medium containing at least one caspase inhibitor that inhibits cleavage of poly(ADPribosyl) polymerase (PARP-1), wherein the inhibitor concentration is between 80 μM to 200 μM; and
    yielding the population of multipotent cells.

2. The method of claim 1 wherein the medium for culturing human embryonic stem cells into a population of multipotent cells includes mammalian serum.

3. The method of claim 1 wherein the at least one inhibitor is a tetrapeptide inhibitor.

4. The method of claim 3 wherein the tetrapeptide inhibitor is N-benzyloxycarbonyl-Asp-Glu-Val-Asp fluoromethylketone (DEVD.FMK).

5. A multipotent cell population, wherein at least 75% of the cells are Oct4 negative, and exhibit uniform, spindle shaped-morphology with a small nucleus, reduced caspase activity, reduced ability to bind Annexin-V, and increased expression of mesoderm and endoderm genes selected from the group consisting of brachyury variant A, BMP4, GATA-3, WNT5A, WNT3, Nodal, Scl, Flk and DKK4 relative to a population of human embryonic stem cells.

6. The cell culture of claim 5, wherein over 90% of the cells in the culture test negative for caspase-3 activity.

7. The method of claim 1 wherein the at least one inhibitor inhibits caspase-3 activity.

8. The method of claim 1 wherein at least 75% of the multipotent cells in culture are Oct4 negative, and exhibit uniform, spindle shaped morphology with a small nucleus, reduced caspase activity, reduced ability to bind Annexin-V, and increased expression of mesoderm and endoderm genes, selected from the group consisting of brachyury variant A, BMP4, GATA-3, WNT5A, WNT3, Nodal, Scl, Flk and DKK4 relative to human embryonic stem cells.

9. A method of producing a population of multipotent cells comprising the steps of
    a) providing a culture of human embryonic stem cells;
    b) culturing the cell population of step (a) for 2 to 3 days in a culture medium containing at least one caspase inhibitor that inhibits cleavage of poly(ADPribosyl) polymerase PARP-1), and inhibits caspase-3 activity, wherein the inhibitor concentration is between 80 μM to 200 μM; and
    (c) yielding the population of multipotent cells.

10. The method of claim 1 or 9 wherein the inhibitor is a peptide inhibitor.

11. The method of claim 9 wherein the inhibitor is a tetrapeptide inhibitor.

12. The method of claim 11 wherein the tetrapeptide inhibitor is N-benzyloxycarbonyl-Asp-Glu-Val-Asp fluoromethylketone (DEVD.FMK).

* * * * *